United States Patent
D'Angelo

[11] Patent Number: 5,925,603
[45] Date of Patent: Jul. 20, 1999

[54] STABLE LIQUID DELIVERY SYSTEM FOR ACYL ISETHIONATES

[75] Inventor: Paul F. D'Angelo, Princeton, N.J.

[73] Assignee: Rhodia Inc., Cranbury, N.J.

[21] Appl. No.: 08/990,491

[22] Filed: Dec. 15, 1997

Related U.S. Application Data

[60] Provisional application No. 60/032,447, Dec. 19, 1996.

[51] Int. Cl.$^6$ .............................. C11D 1/88; C11D 1/94; C11D 1/12

[52] U.S. Cl. ..................... 510/119; 510/125; 510/130; 510/235; 510/490; 510/405; 510/409; 510/414; 510/422; 510/428; 510/496

[58] Field of Search .................. 510/119, 125, 510/130, 235, 490, 405, 409, 414, 422, 428, 496

[56] References Cited

U.S. PATENT DOCUMENTS

| | | | |
|---|---|---|---|
| 4,243,549 | 1/1981 | Messenger et al. | 252/355 |
| 4,777,038 | 10/1988 | Scheuffgen | 424/70 |
| 5,013,473 | 5/1991 | Norbury et al. | 252/174.13 |
| 5,275,755 | 1/1994 | Sebag et al. | 252/174.15 |
| 5,372,751 | 12/1994 | Rys-Cicciari et al. | 252/554 |
| 5,409,640 | 4/1995 | Giret et al. | 252/546 |
| 5,415,810 | 5/1995 | Lee et al. | 252/545 |
| 5,490,955 | 2/1996 | Hagan et al. | 252/554 |
| 5,518,647 | 5/1996 | Zocchi | 252/174.17 |
| 5,529,721 | 6/1996 | Salka et al. | 252/546 |
| 5,536,493 | 7/1996 | Dubief et al. | 424/70.13 |
| 5,560,873 | 10/1996 | Chen et al. | 510/123 |
| 5,614,473 | 3/1997 | Dino et al. | 507/202 |
| 5,716,920 | 2/1998 | Glenn, Jr. et al. | 510/159 |
| 5,747,435 | 5/1998 | Patel | 510/119 |
| 5,756,439 | 5/1998 | He et al. | 510/159 |

FOREIGN PATENT DOCUMENTS

| | | | |
|---|---|---|---|
| 0 692 240 A1 | 1/1996 | European Pat. Off. | A61K 7/00 |
| 0692240 | 1/1996 | European Pat. Off. | A61K 7/00 |
| 2297762 | 8/1996 | United Kingdom | C11D 1/74 |
| WO 9532705 | 7/1995 | WIPO | A61K 7/50 |
| 0662316 | 12/1995 | WIPO | A61K 7/06 |

OTHER PUBLICATIONS

P. J. Petter, "Fatty Acid Sulphoalkylamides and Esters as Cosmetic Surfactants", *International Journal of Cosmetic Science*, 6, 249–260 (1984).

C. Fox, "Technically Speaking", *Cosmetics and Toiletries Magazine*, vol. 111 (3 pages) Jul. 1996.

*Primary Examiner*—Mark Kopec
*Assistant Examiner*—Charles Boyer
*Attorney, Agent, or Firm*—John Daniel Wood; Andrew M. Solomon

[57] ABSTRACT

Concentrated mixtures of three or more surfactants dissolved or dispersed in a stable form in water and which contain an acyl isethionate, an imidazoline surfactant, and at least one additional anionic surfactant are provided.

15 Claims, No Drawings

STABLE LIQUID DELIVERY SYSTEM FOR ACYL ISETHIONATES

CROSS-REFERENCE TO RELATED APPLICATIONS

This application claims priority from U.S. Ser. No. 60/032,447, filed Dec. 19, 1996, the disclosure of which is incorporated by reference herein.

BACKGROUND OF THE INVENTION

This invention relates to storage stable liquid delivery systems (LDS) for acyl isethionates. A typical acyl isethionate is sodium cocoyl isethionate (SCI) and it will be used as the reference isethionate for this invention.

Besides the SCI, two other critical components in the LDS of this invention are an imidazoline amphoteric (IA) and a second anionic surfactant (SAS) or combination of SAS's. Both are described later in this specification. The SCI is viewed as the main or primary anionic surfactant.

The LDS of this invention are suitable for use in the preparation of water based detergent formulations. For example, in personal care applications, the LDS can be letdown with water to prepare hair shampoos, hand soaps, facial cleaners, bath gels and foams, shower gels and body washes. In these formulations, the LDS are expected to impart good detergency and mildness to the skin and hair, provide good foam volume and quality and generate a creamy lather when applied to the skin or hair.

The LDS are free standing liquids at 25° C. They can be made by a number of processes, but typically in this invention are made by mixing the surfactants in water at elevated temperatures until a clear solution forms and then cooling the LDS typically to 25° C. and holding at this temperature. We reference here patent application Ser. No. 08/641,124, filed on Apr. 30, 1996 and assigned to Rhône-Poulenc Inc. which describes a unique process to make LDS of this invention. In that process, molten acyloxyalkane sulfonate (which is the crude reaction product of acylating an alkane sulfonic acid with a fatty acid) is quenched in an aqueous quench liquid comprised of an amphoteric and/or an anionic surfactant to produce a blend of the acyloxyalkane sulfonate and amphoteric and/or anionic surfactant. To the extent necessary for completion, this application is expressly incorporated by reference.

In order to deliver SCI in a water-based LDS, one must overcome the major physical property obstacle of SCI: its very limited water solubility. At 25° C., it is soluble at 0.01% by weight. It is surprising that one can make SCI based LDS that can contain SCI concentrations that are over 1000 times its water solubility at 25° C.

The LDS can be clear, translucent, or opaque liquids at 25° C. The appearance is primarily dependent on the concentration of SCI and the ratio of SCI to other contained surfactants; the pH of the system can also play a role. At 25° C., the LDS are flowable liquids that are pourable and pumpable in many cases. At 25° C., these flowable LDS have viscosities typically at or below 30000 cps.

At elevated temperatures (35–50° C.), the LDS remain as flowable liquids. If they are opaque at 25° C., they can become clear or translucent systems between 35–50° C. No precipitation of particulate solids or loss of clarity occurs in the LDS when exposed both to elevated temperatures and a broad pH range (6.0–9.0). At high temperatures and pH above 8.0, SCI can potentially become hydrolytically unstable and one would expect to see precipitation of solid matter, loss of clarity and/or gel formation. None of these effects occur in the inventive LDS after typical exposure periods. By reference, please compare the article by P. J. Petter, "Fatty Acid sulphoalkylamides and Esters as Cosmetic Surfactants," *International J. of Cosmetic Science*, 6, 249–260 (1984).

Typically the inventive LDS are maintained at pHs equal to 7 or greater, more typically from pH=7.5–8.5, and most typically for pH=7.8–8.2. In the most typical pH range, the SCI is hydrolytically stable, the outstanding hydrotroping and solubilizing power of the IA is maintained, and the LDS viscosity is such that they are pourable and in many cases pumpable systems and are typically storage stable over a wide temperature regime. Of course, pH's at or below 7.0 can be used, but the overall beneficial properties of our LDS are best exhibited at pHs above 7.0.

At temperatures below 25° C., e.g. 4–22° C., the LDS of this invention containing low to moderate amounts of SCI typically are opaque, flowable liquids, but LDS with high SCI contents are typically opaque, nonflowable creams, pastes or gels. These nonflowable systems can become flowable again by heating them to slightly elevated temperatures (30–45° C.); in many cases these nonflowable, opaque systems will not only become flowable at these elevated temperatures, but clear as well.

Two component LDS that contain an SCI and an IA or a betaine can be made but these suffer from a number of technical limitations. Rhône-Poulenc's application Ser. No. 08/641,124, filed on Apr. 30, 1996 describes in part two component systems. In this application, one can see that at ambient conditions, these two component systems are typically pastes or very viscous liquids that appear to require relatively high loadings of the IA or betaine to effect SCI solubility. It would be impractical to work with these very viscous liquids and pastes in making personal care or other detergent formulations. Easily flowable, two component systems would either have a commercially unattractively low total active content (<25%) or would have too low of an IA or betaine content that could solubilize SCI concentrations that would be commercially attractive ($\geq 12\%$).

In addition, solubilizing the SCI by the IA or betaine in liquid two component systems requires a relatively high weight ratio of IA or betaine to SCI, typically greater than one. For example, in personal care formulation where the SCI to IA or betaine actives ratio needs to be equal to or greater than one, additional SCI would have to be added and heated to high temperatures (70–90° C.) to dissolve it; this heating step defeats the purpose of creating LDS, which should not require or require only modest heating (30–40° C.) when formulating personal care formulations.

Overall, two component LDS are either impractical to handle; or if handleable, would be expected to have too low an active concentration for commercial interest; or unstable in that useful amounts of SCI in the two component LDS would precipitate at ambient conditions because of insufficient IA or betaine content.

In this invention, surprisingly, we have found that replacing some of the IA with an SAS or adding an SAS to a two component LDS largely overcomes the above limitations.

LDS containing significant quantities of organic surfactant that have limited water solubility at room temperature such as SCI are relatively rare, but do exist. For example, they are sold under the tradename MIRASHEEN licensed to Rhône-Poulenc, Inc. and EUPERLAN licensed to Henkel. In these LDS, ethylene glycol mono and/or distearate, which are essentially insoluble in water at 25° C., are dispersed in a stable form in water at room temperatures by the presence of suitable emulsifying type surfactants. These LDS are opaque at ambient conditions. By reference, U.S. Pat. Nos. 5,529,721, 4,777,038 and 5,560,873 are included as recent examples.

By contrast, no comparable LDS containing the compositions of this invention are known to be manufactured and sold under a commercial tradename.

We are aware that formulated liquid personal care products may contain a combination of surfactants that are covered in this invention. However, these formulated products may use any one of them, e.g. SCI, at very low actives concentration and the total surfactant active concentration is generally below the lower limit of the actives content of this invention. By reference, U.S. Pat. No. 5,518,647 (Colgate) and EP692240 (L'Oreal) are included as examples.

Formulators of personal care and other household detergent products will find many advantages in using LDS. First, they enhance formulation quality through consistent performance of the surfactant mixture; second, they reduce batch adjustment and cycle times to make the formulations; third, they provide cold or low heat mixing opportunities thereby reducing and/or eliminating high energy heating processes; fourth, they allow for increased plant throughput and overall reduction in energy and manpower costs; fifth, quality control time is reduced with the elimination of many individual surfactants to purchase and monitor; sixth, handling costs through consolidated warehousing, bulk storage, and elimination of partial drums are decreased; and seventh, most solids and viscous liquids are eliminated. In addition for SCI based LDS, the irritancy of SCI dust particles is eliminated as a potential health hazard.

Some literature relates to surfactant mixtures containing SCI. U.S. Pat. No. 5,415,810 relates to the use of zwitterionic surfactants such as simple betaines, amidobetaines, and sulphobetaines and is not directed toward the use of an IA; in fact, no direct mention of an IA can be found. In addition, U.S. Pat. No. 5,415,810 does not direct itself toward stable, free standing surfactant mixtures but instead immediately incorporates the mixtures into a personal care product where the SCI is stabilized by a variety of well-known additives used in personal care products and where the SCI and other surfactants are diluted in water for enhanced solubility.

In U.S. Pat. No. 4,243,549 are described highly concentrated mixtures of anionic and imidazoline amphoterics among other mixtures. However, U.S. Pat. No. 5,243,549 is directed toward concentrated mixtures whose surfactant actives are essentially above 60% by weight and the mixture is predominantly in the lamellar or "G" phase. In addition, U.S. Pat. No. 4,243,549 directs itself toward anionic surfactants such as alkyl ether sulfates which are soluble in substantial amounts in water and is not directed toward SCI which are marginally soluble in water at ambient conditions. LDS of this invention have surfactant actives of 50% by weight or less and are predominantly if not completely outside of the "G" phase.

Other literature exists which show the utility of SCI in combination with an IA and a second anionic surfactant (SAS). However, the products described therein are outside the scope of this invention because the total surfactant actives is less than that of this invention; the percent SCI or IA is less than that of this invention; the percent of SCI plus IA is less than that of this invention; the SAS is greater in concentration than that of this invention and/or the products described are solids, not liquids. Some patents as previously referenced are U.S. Pat. Nos., 5,372,751, 5,518,647 and EP692240.

SUMMARY OF THE INVENTION

LDS of this invention are concentrated mixtures of three or more surfactants dissolved or dispersed in a stable form in water and contain an acyl isethionate, an imidazoline surfactant, and at least one additional anionic surfactant. They are clear, translucent, or opaque liquid systems, that are pourable and pumpable in many cases at 25° C. They can be stored for extended periods at room, elevated and cold temperatures without precipitation or decomposition of SCI though some systems will become nonflowable creams, pastes or solids at cold temperatures. Flowabiltiy can be regenerated by heating them to slightly elevated temperatures (30–45° C.). They are stable over a broad pH range, but typically pHs in the range 7.0–8.5 are employed to optimize the stability and flowability of the LDS.

We believe the LDS of this invention are new, useful and unobvious to those skilled in the art of making stable surfactant mixtures, particularly those mixtures containing SCI, which has very limited water solubility at 25° C.

DETAILED DESCRIPTION OF THE INVENTION

This invention provides LDS which contain 10 to 50% of surfactant actives, and the surfactant actives mixture contained therein is comprised of:

(a) 10–60% by weight of an alkali and/or alkaline earth acyl isethionate of the form:

$$R_1CO_2(CH_2)nSO_3^-M^+ \qquad (I)$$

where $R_1$ is hydrocaryl radical from 6–26 carbons, n is an integer from 2 to 4, preferably 2, and M is an alkali or alkali earth metal such as sodium, potassium, lithum and magnesium, preferably sodium.

(b) 10 to 80% of an imidazoline amphoteric surfactant of the following form:

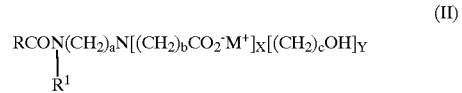

$$\text{RCON(CH}_2)_a\text{N}[(\text{CH}_2)_b\text{CO}_2^-M^+]_X[(\text{CH}_2)_c\text{OH}]_Y \qquad (II)$$
$$\underset{R^1}{|}$$

where a=1–3;
b, c are the same or different and are 1, 2, or 3;
M is an alkali or alkali earth metal;
X=1 or 2, Y=0, 1, X+Y=2,
$R^1$ =H or $CH_2CH_2OH$
R=alkyl or alkylene radical for 6 to 26 carbons
or of the form:

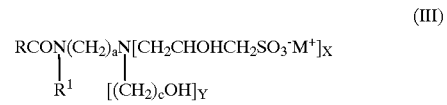

$$\text{RCON(CH}_2)_a\text{N}[CH_2CHOHCH_2SO_3^-M^+]_X \qquad (III)$$
$$\underset{R^1}{|} \quad \underset{[(CH_2)_cOH]_Y}{|}$$

where R, $R^1$, a, c, M, X, Y have the same meaning as for (II)

(c) 5 to 55% of a second anionic surfactant or mixture of second anionic surfactants wherein the weight of (a) is no more than four times the weight of (b) and the weight of (a) plus (b) in the mixture is from 45 to 90%.

The surfactants that are part of this invention are described in detail below.

Acyl Isethionates

The acyl isethionate is of the form:

$$R_1-C(O)-O(CH_2)_n SO_3^- Y^+ \qquad (I)$$

wherein $R_1$ is a hydrocarbyl radical, desirably from about 6 to 26 carbon atoms, n is integer from 2 to 4, preferably 2 and Y is an alkali metal or alkaline earth metal, more particularly, sodium, potassium, lithium or magnesium and preferably sodium. The alkaline portion of the sulfonates of Formula I for use herein includes ethylene and branched or unbranched propylene or butylene. The fatty alkyl moiety R1 is a hydrocarbyl containing from about 6 to about 26 carbon atoms and preferably from about 6 to about 20 carbon atoms such as hexanoic, octanoic, decanoic, dodecanoic, lauric, behenic, palmitic, stearic, myristic, arachidic, oleic, linolenic, linoleic and the like including mixtures of the foregoing as in the particularly preferred cocoyl derivatives from coconut oil fatty acids. Fatty acids from natural sources are comprised of numerous fatty acids that all generally fall within the stated carbon range. A small proportion of mono- or di-unsaturated fatty acid derivatives may be desirable to provide adequate foaming and solubility in blends containing the neat soap. Normally, the degree of unsaturation will not be less than about 2 or more than 12, when measured by iodine number. It will be observed in this context that the term "hydrocarbyl" is intended to embrace linear and branched aliphatic radicals that include alkyl, alkenyl, alkynyl, and alkadienyl moieties. Too large a proportion of unsaturation, tends to render the sulfonate susceptible to oxidative degradation. The preferred compounds are acyl isethionates, preferably cocoyl isethionates.

The acyloxyalkane sulfonates are prepared by the direct esterification of a hydroxyalkane sulfonic acid with a fatty acid. The reaction can be conducted using well documented procedures. Temperatures of reaction are sufficient to effect reaction and maintain the product molten but not sufficiently high to cause substantial decomposition under normal product working conditions. Temperatures within the range of from about 180° C. to about 250° C. have been found to be effective. Since excess fatty acid is used as solvent, the molten reaction mixture contains the desired product along with excess fatty acid and sulfonate reaction material impurities. The reaction is conducted for a period of time sufficient to achieve conversation but insufficient to allow substantial product degradation, for example from about 1 to about 8 hours.

Acyl isethionates will contain some free fatty acid ($\leq 10\%$ by weight) and a little unreacted metal isethionate. Typically, the acyl isethionate comprised 80–85% of the total organic isethionate.

Acyl isethionates are known to be very mild detergents, provide good to excellent foam volume and quality, and generate a rich, creamy lather in personal care products. Even relatively small amounts of acyl isethionate can contribute to these benefits. In U.S. Pat. No. 5,415,810 assigned to Lever Brothers Company, it is stated on column 2, line 10, that "fatty low levels will contribute these benefits" and in example 13, a hand washing composition is shown with 2% by weight SCI, indicating that even at 2% by weight loading can contribute the above benefits. Acyl isethionates are sold under the tradename GEROPON from Rhône-Poulenc, Inc. and JORDAPON from PPG Industries.

SCI has very poor water solubility (0.01% by weight in distilled water at 25° C.) and is considered to be hydrolytically unstable in hot water (>50° C.) above pH=8.0. To provide the benefits of SCI in liquid personal care formulations, we need to improve its water solubility or stable dispersibility at least a factor of 200, preferably a factor of 500, and most preferably a factor of 1000. We can accomplish this improved solubility or dispersibility by combining SCI with an imidazoline amphoteric surfactant and an anionic or combination of anionic surfactants.

In this invention, SCI can be soluble or dispersible in the LDS from 2.5% to 30% by weight, preferably from 8 to 20% by weight, and most preferably from 12–18% by weight, based on the weight of the entire composition. In the most preferred range, we have stable and flowable LDS over a wide temperature and pH range and sufficient concentration of SCI to provide the performance benefits of SCI in most personal care and other detergent products.

Imidazoline Amphoterics

In a generalized scheme, an imidazoline amphoteric (IA) or alkyl amphoglycinate is made by the following process. For (II) where b=1, a fatty acid is reacted with an amino ethyl ethanolamine (AEEA) at elevated temperatures (200° C.) to produce a fatty acid imidazoline (IV).

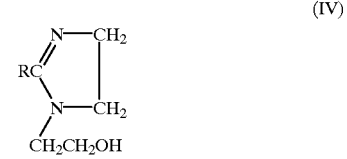

(IV)

The imidazoline is then reacted with an alkali monochloroacetate such as sodium monochloroacetate (SMCA) to form the alkali fatty amphoglycinate under basic conditions and at elevated temperatures (80° C.). The final product contains minor amounts of inorganic salt, glycolates and amidoamines among other byproducts. The concentration of the glycinate in water would typically be from 30- to 40% by weight.

Alkyl amphopropionates (II, b=2) are formed by reacting IV with an alkyl acrylate such as methyl acrylate under basic conditions to give mono or dipropionates. The alkyl amphosulfonates (III) such as an alkyl amphopropylsulfonate are formed by reacting IV with epichlorohydrin in the presence of a bisulfite.

The amphoglycinates, amphopropionates, and amphosulfonates are sold under the tradename MIRANOL licensed to Rhône-Poulenc, Inc. Examples of commercial products are MIRANOL ULTRA C-32, MIRANOL HMA, MIRANOL CM-SF Concentrate, and MIRANOL CS Concentrate respectively.

The SCI (I) to IA (II, III) actives ratio can be from 4:1 to 1:4; preferably from 3:1 to 1:3 and most preferably from 2:1 to 1:1. In the most preferred range, we have flowable LDS which are stable over a wide temperature and pH range which have SCI to IA actives ratio that provide excellent formulation flexibility for personal care products.

The IA actives can be added to LDS from 3 to 30% by weight, preferably from 4 to 20% by weight and most preferably from 6 to 12% by weight, based on the weight of the entire composition.

Second Anionic Surfactant (SAS)

A second or combination of second anionic surfactants are part of the LDS of this invention. These SAS's include alkyl taurates, alkyl ether sulfates, alkyl or alkenyl sulfates, alkyl glyceryl ether sulfates, sulphosuccinates, sulfosuccinamates, sarcosinates, sulphoacetates, monoalkyl phosphate esters, di-alkyl phosphate esters, mono-alkyl ether phosphate esters, di-alkyl ether phosphate esters, alpha-olefin sulfonates, acyl lactates, alkyl ether carboxylates and glyceryl ether carboxylates.

Individually or in combination, these SAS can be added to LDS containing SCI and an IA and are selected for their solubilizing, viscosity controlling and/or mildness properties.

As we have previously stated, in order for an IA to solubilize SCI in reasonable quantities ($\geq 12\%$ by weight), the two component LDS were typically extremely viscous liquids, creams, pastes or solid opaque gels; consequently they were pourable with great difficulty, nonpourable and/or nonpumpable at 25° C. On the other hand, if relatively low concentrations of IA were used to improve the flowability, the two component LDS were unstable, i.e. precipitation of SCI occurred at 25° C.

We have found that by adding or replacing part of the IA with one or a combination of SAS's in two component LDS, we can generate LDS which are pourable and pumpable in many instances and stable at 25° C., in that no precipitation of SCI occurs. While stable, two components LDS with actives contents at commercially attractive amounts, i.e. 25% or greater, typically have viscosities in excess of 50,000 cps at 25° C. or are nonpourable creams, pastes or gels, the LDS of this invention typically have viscosities below 30,000 cps, and in many cases, below 10,000 cps, where we would expect LDS of this invention to be pumpable.

We believe adding one or more SAS's to provide the cited improvements to two component LDS is unexpected and would be unobvious to those skilled in the art of making stable, water-based surfactant mixtures, particularly mixtures containing useful concentrations of SCI. Since we are in many cases partially replacing IA, which is an excellent hydrotrope or solubilizing surfactant, with an SAS, which is generally considered to be less of a hydrotrope or solubilizing surfactant than IA, these results are particularly unexpected and unobvious.

While all the SAS's of this invention can provide some of the cited improvements to two component systems, certain SAS's are particular attractive because of their good to excellent solubilizing of SCI, viscosity controlling properties, inherent mildness and/or lower cost of manufacture among other attributes. These include alkyl taurates, alkyl ether sulfates, sulfosuccinates, alpha olefin sulfonates, sarcosinates, and monoalkyl ether phosphates.

N-alkyl taurates are of the form:

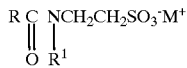  (V)

where R is an alkyl or alkyl group of 8 to 22 carbons and $R^1$ is an alkyl or alkenyl group of 1–4 carbons. M is typically an alkali or alkaline earth metal.

Alkyl or alkenyl ether sulfates are of the form:

$$RO(CH_2CH_2O)_xSO_3^-M^+ \quad (VI)$$

where R and M have the same meaning as above and X=1–12 units.

Sulfosuccinates are of the form:

$$RO_2CCH_2CH(SO_3^-M^+)CO_2^-M^+ \quad (VII)$$

and $$R\ CONHCH_2CH_2O_2CCH(SO_3^-M^+)CH_2CO_2^-M^+ \quad (VIII)$$

and $$R(OC_2H_4)_xO_2C\ CH(SO_3^-M^+)CH_2CO_2^-M^+ \quad (IX)$$

where R and M and X have the same meaning as above.

Alpha olefin sulfonates are of the form:

$$CH_3(CH_2)_nCH=CH\ CH_2SO_3^-M^+ \quad (X)$$

where M has the same meaning as above and n=1–18 units.

Sarcosinates are of the form:

$$R\ CON(CH_3)CH_2CO_2^-M^+ \quad (XI)$$

where R and M have the same meaning as above.

Monoalkyl ether phosphates are of the form:

$$[RO(CH_2CH_2O)_n]PO_2^-M^+ \quad (XII)$$

where R and M have the same meaning as above and n=1–12 units.

The second anionic surfactant is typically added to the LDS in an amount of at least about 0.5% by weight, more typically at least about 1.5% by weight, and even more typically at least about 3% by weight, e.g. from about 5% by weight to about 10% by weight, based on the weight of the entire composition.

Optional Ingredients for LDS of the Invention

To further enhance the pourability, stability and/or performance of LDS in detergent products, minor amounts of other anionic surfactants that are believed to be less mild to the skin and hair than the anionic surfactants used in this invention may be added. They may be present at five percent by weight or less, more typically on the order of 1–2% by weight. These anionics include alkylaryl sulfonates such as alkyl benzene sulfonates and xylene sulfonates.

Nonionic surfactants may also be added at or below 5% by weight, typically 1–2% by weight, to enhance pourability, stability and/or performance. For some surfactants, they may also provide opacity and pearlescence. When adding some of these nonionics, care must be taken not to diminish the foaming and lathering properties of the LDS. Nonionic surfactants include alkanolamides, ethylene glycol monostearate, ethylene glycol distearate and alkyl ethoxylated alcohols and alkyl ethoxylated/propoxylated alcohols.

Zwitterionic surfactants may also be added at or below 5% by weight, typically 1–2% by weight to the surfactant mixture to provide primarily foam boosting and/or conditioning properties. Zwitterionics include simple betaines, amidobetaines, sulphobetaines, alkyl iminoacetates, alkyliminodiacetates, alkyl iminopropionates, alkyl iminodipropionate, and alkyl amine oxides.

Very small amounts of other chemical may be added to the LDS of this invention. These additives include but are not necessarily limited to pH adjusting chemicals such as acids, bases and buffers, e.g. sodium hydroxide, citric acid, triethanolamine; lower molecules weight alcohols containing more than one hydroxyl group, e.g. ethylene glycol, propylene glycol, diethylene glycol, triethylene glycol, glycerin; antioxidants, e.g. BHT; preservatives, e.g. methyl and propyl parabens and the like; inorganic salts, e.g. alkali and alkali metal halides, acetates, carboxylates, sulfonates, and citrates; thickening and conditioning agents such as guar and cellulosics and chemical derivatives of guar and cellulosics.

The above compositions are particularly suited for use in personal care and household detergent care applications such as solid or liquid cleaning compositions, shampoos, hand soaps, body washes, dishwashing detergents, fabric detergents, hard surface cleaning compositions and the like.

The following examples will serve to illustrate the invention, but should not be construed to limit the invention. All parts, percentages, ratios and the like in these examples and in the remainder of the specification and claims are by weight unless noted otherwise.

EXAMPLES

Comparative Example 1

This example shows that two component LDS, which are not part of the invention, are impractical systems for commercialization in that they either precipitate SCI, are too viscous or are nonpourable creams, pastes or gels, have relatively low actives content, and/or have IA to SCI actives ratio that are typically greater than one and thereby limit the formulation of personal care and other detergent formulations to products where the SCI concentration will be below the IA concentration unless one adds more SCI at high temperatures (70–90° C.) to incorporate it into the formulation. This addition of SCI at high temperatures in essence defeats the purpose of LDS.

pumpable in many cases and are stable at 25° C. in that no precipitation of SCI occurs. In addition many have SCI to IA actives ratio greater than one, which provides formulators of personal care and other detergent products with much wider formulation latitude compared to the two component systems in Table 1.

LDS in Table 2 were made by adding the IA and liquid SAS to water, then heating to 90° C., adding the SCI, mixing until a clear solution occurs, and then cooling and equilibrating to 25° C., followed by pH adjustment. If the SAS is a solid, then both the SAS and SCI are added to 90° C. and dissolved to a clear solution followed by cooling to 25° C.

TABLE 1

COMPARATIVE EXAMPLE 1

| COMPOSITION | 1-A | 1-B | 1-C | 1-D | 1-E | 1-F | 1-G | 1-H |
|---|---|---|---|---|---|---|---|---|
| SCI[1] | 12.0 | 12.0 | 12.0 | 12.0 | 15.0 | 15.0 | 18.0 | 18.0 |
| IA[2] | 21.0 | 30.5 | 47.0 | 60.0 | 40.0 | 60.0 | 32.0 | 52.5 |
| WATER | 67.0 | 57.5 | 41.0 | 28.0 | 45.0 | 25.0 | 50.0 | 29.0 |
| INITIAL APPEARANCE (25° C.)[3] | Clear, water thin liquid with precipitate | Hazy thin liquid with precipitate and gel-like particles | Clear viscous liquid | Clear, viscous Liquid | Opaque, viscous liquid | Opaque gel | Opaque gel | Opaque gel |
| Viscosity (cps, 25° C.) | — | — | 55000 | 85000 | 70000 | — | — | — |
| Wt. % SCI + IA Actives | 17 | 20 | 25 | 29 | 25 | 32 | 25 | 32 |
| SCI/IA Actives Ratio | 1.5 | 1.0 | 0.66 | 0.55 | 1.0 | 0.65 | 1.5 | 0.9 |

1. Added as GEROPON AC-78NP (Rhône-Poulenc), 80–85% actives sodium cocoyl isethionate.
2. Added as MIRANOL ULTRA C-32 (Rhône-Poulenc), 32% active sodium cocoamphoacetate.
3. pHs for all LDS was adjusted to 8.0 ± 0.2.

Example 2

LDS of this invention were made and are shown in Table 2. They overcome the limitations of two components LDS described in Example 1. They are all pourable liquids and

TABLE 2

EXAMPLE 2

| COMPOSITION | 2-A | 2-B | 2-C | 2-D | 2-E | 2-F | 2-G | 2-H |
|---|---|---|---|---|---|---|---|---|
| SCI[1] | 8.4 | 12.0 | 12.0 | 15.0 | 15.0 | 18.0 | 18.0 | 20.0 |
| IA[2] | 30.0 | 30.0 | 30.0 | 25.0 | 25.0 | 20.0 | 20.0 | 30.0 |
| ACYL TAURATE[3] | 16.6 | 12.0 | — | 9.0 | — | 12.0 | — | 10.0 |
| ALKYL ETHER SULFATE[4] | — | — | 30.0 | — | 30.0 | — | 40.0 | — |
| WATER | 45.0 | 46.0 | 28.0 | 51.0 | 30.0 | 58.0 | 22.0 | 40.0 |
| INITIAL APPEARANCE (25° C.)[5] | Clear liquid | Opaque liquid | opaque liquid | Opaque liquid | Opaque liquid | translucent liquid | translucent liquid | translucent liquid |
| VISCOSITY (cps, 25%) | 50 | 200 | 5000 | 700 | 9000 | 500 | 5500 | 18000 |
| SCI + IA + SAS WT. % ACTIVES | 29 | 29 | 29 | 28 | 27 | 30 | 33 | 34 |
| SCI/IA ACTIVE RATIO | 0.7 | 1.0 | 1.0 | 1.3 | 1.3 | 2.3 | 2.3 | 1.7 |

1. Added as GEROPON AC-78NP (Rhône-Poulenc), 80–85% actives sodium cocoyl isethionate.
2. Added as MIRANOL ULTRA C-32 (Rhône-Poulenc), 32% active sodium cocoamphoacetate.
3. Added as GEROPON TC-270, a 80% active sodium cocomethyl taurate (Rhône-Poulenc).
4. Added as RHODAPEX ES, a 30% actives sodium laureth(3) sulfate (Rhône-Poulenc).
5. pH's were adjusted to 8.0 ± 0.2.

Example 3

The LDS of Table 2 were stored at 4° C., 25° C. and 45° C. for one month. Their appearance was observed initially (Table 2) and after one month. Their appearance after storage for one month at these temperatures is shown in Table 3. All LDS stored at 25° C. retain their initial appearance (Table 2). LDS stored at 45° C. became clear or translucent liquids; no precipitation of any solid matter was observed at 45° C storage. At 4° C., all LDS became opaque. Most became creams, pastes or solid gels; a few remained liquids. LDS stored at 4° C. for one month were heated to 30–40° C. with gentle mixing to make them clear or translucent and when cooled to 25° C., their initial appearance at 25° C. was regenerated.

TABLE 3

EXAMPLE 3
Appearance of LDS in Table 2 Stored at 4° C., 25° C. and 45° C. for One Month

| LDS | 4° C.[1] | 25° C. | 45° C. |
| --- | --- | --- | --- |
| 2-A | Opaque liquid | Clear liquid | Clear liquid |
| 2-B | Opaque liquid | Opaque liquid | Clear liquid |
| 2-C | Opaque liquid | Opaque liquid | Clear liquid |
| 2-D | Opaque cream | Opaque liquid | Clear liquid |
| 2-E | Opaque paste | Opaque liquid | Clear liquid |
| 2-F | Opaque paste | Translucent liquid | Clear liquid |
| 2-G | Opaque solid | Translucent liquid | Clear liquid |
| 2-H | Opaque solid | Translucent liquid | Clear liquid |

1. 2A-2H stored at 4° C. for one month were heated from 30–40° C. with gentle mixing and became clear to translucent, pourable liquids.

Example 4

A variety of SAS's can be added to or replace in part an IA in two component LDS. Table 4 shows LDS of this invention which contain a broad range of SAS's. These LDS are stable and flowable liquids at 25° C. These LDS were also stored at 4° C., 25° C. and 45° C. for one month. Results of one month storage as shown in Table 5.

TABLE 4

EXAMPLE 4

| COMPOSITION | 4-A | 4-B | 4-C | 4-D | 4-E | 4-F |
| --- | --- | --- | --- | --- | --- | --- |
| SCI[1] | 15.0 | 15.0 | 15.0 | 15.0 | 15.0 | 15.0 |
| IA[1] | 25.0 | 25.0 | 25.0 | 25.0 | 25.0 | 25.0 |
| Alkyl Ether Sulfate[3] | 30.0 | — | — | — | — | — |
| Ethoxylated Carboxylate[4] | — | 7.0 | — | — | — | — |
| Alkyl Ether Phosphate[5] | — | — | 5.0 | — | — | — |
| Alpha-Olefin Sulfonate[6] | — | — | — | 22.0 | — | — |
| Sulfosuccinate[7] | — | — | — | — | 30.0 | — |
| Alkyl Sulfate[8] | — | — | — | — | — | 30.0 |
| Water | 30.0 | 53.0 | 55.0 | 38.0 | 30.0 | 30.0 |
| Initial Appearance (25° C.) | Translucent liquid | Opaque liquid | Clear liquid | Opaque liquid | Clear liquid | Clear liquid |
| Viscosity (25° C., cps) | 5000 | 200 | 30000 | 500 | 24000 | 30000 |
| Wt. % Actives (SCI + IA + SAS) | 30 | 27 | 26 | 29 | 30 | 30 |
| SCI/IA Actives Ratio | 1.6 | 1.6 | 1.6 | 1.6 | 1.6 | 1.6 |

1. Added as GEROPON AC-78NP (Rhône-Poulenc), 80–85% actives sodium cocoyl isethionate.
2. Added as MIRANOL ULTRA C-32 (Rhône-Poulenc), 32% active sodium cocoamphoacetate.
3. Added as RHODAPEX ESY, a 30% active sodium laureth(1) sulfate (Rhône-Poulenc).
4. Added as MIRANATE LEC-80, an 80% active sodium laureth (13) Carboxylate (Rhône-Poulenc)
5. Added as RHODAFAC PC-100, a 98% actives monoalkyl ether phosphate (Rhône-Poulenc).
6. Added as RHODACAL A-246L a 40% active alpha olefin sulfonate (Rhône-Poulenc).
7. Added as GEROPON SBFA-30, a 30% active disodium laureth (3) sulfosuccinate (Rhône-Poulenc).
8. Added as RHODAPON SB-8208S, a 30% actives sodium lauryl sulfate (Rhône-Poulenc).

TABLE 5

EXAMPLE 4

Appearance of LDS in Table 4 Stored at 4° C., 25° C. and 45° C. for One Month

| LDS | 4° C.[1] | 25° C. | 45° C. |
| --- | --- | --- | --- |
| 4-A | Opaque cream | Opaque liquid | Clear liquid |
| 4-B | Opaque liquid | Opaque liquid | Clear liquid |
| 4-C | Opaque cream | Clear liquid | Clear liquid |
| 4-D | Opaque liquid | Opaque liquid | Clear liquid |
| 4-E | Opaque cream | Clear liquid | Clear liquid |
| 4-F | Opaque paste | Clear liquid | Clear liquid |

1. 4A-4F stored at 4° C. for one month were heated from 30–40° C. with gentle mixing and became clear to translucent, pourable liquids.

Example 5

A clear hair shampoo was made using the following formulation:

| Composition | Parts By Weight |
| --- | --- |
| Water | 57.7 |
| LDS (Ex. 4, Composition 4A) | 25.0 |
| RHODAPEX ESY | 15.0 |
| Preservative | 0.1 |
| Fragrance | 0.2 |
| Sodium Chloride | 2.0 |
| Citric Acid | q.s. |

Water, LDS and RHODAPEX ESY were mixed and heated to 30–35° C. to provide a clear system. Preservative and fragrance were added and mixed until dissolved. Salt and citric acid were added to set the final viscosity. Shampoo was cooled to 25° C.

Properties: Viscosity (25° C., cps)=6500; pH (as is)=6.8.

Example 6

A pearlized hand soap was made using the following formulation.

| Composition | Parts by Weight |
| --- | --- |
| Water | 57.7 |
| LDS (Ex. 2, Composition 2E) | 25.0 |
| RHODAPEX SB-8208/S | 10.0 |
| MIRASHEEN 207 | 5.0 |
| Preservative | 0.1 |
| Fragrance | 0.2 |
| Sodium Chloride | 2.0 |
| Citric Acid | q.s. |

The water, LDS and RHODAPON SB-8208/S were added and heated to 30–35° C. to provide clarity and homogeneity of system. MIRASHEEN 207 (a commercial pearlized surfactant concentrate of Rhône-Poulenc) was added and mixed until the system was homogeneous. The preservative and fragrance were added and mixed until dissolved. The salt and citric acid were added to set the final viscosity. The hand soap was cooled to 25° C.

Properties: Viscosity (25° C., cps)=5000, pH (as is)=7.2.

Example 7

A body wash was made using the following formulation:

| Composition | Parts By Weight |
| --- | --- |
| Water | 28.7 |
| LDS (Ex. 2, 2D) | 50.0 |
| RHODAPEX ES | 11.0 |
| MIRANOL ULTRA C-32 | 2.0 |
| MIRASHEEN 207 | 5.0 |
| Preservative | 0.1 |
| Fragrance | 0.2 |
| Sodium Chloride | 3.0 |
| Citric Acid | q.s. |

The water, LDS, RHODAPEX ES and MIRANOL ULTRA C-32 were added and heated to 30–35° C. until a clear system formed. The MIRASHEEN 207 was added and mixed until homogeneous. The preservative and fragrance were added and mixed until dissolved. The salt and citric acid were added to set the final viscosity. Body wash was cooled to 25° C.

Properties: Viscosity (25° C., cps)=11000, pH (as is)=6.7

What is claimed is:

1. Liquid delivery system composition comprising water in an amount from about 50% to about 90% by weight, a cocoyl isethionate in an amount from about 8% to about 20% by weight, an imidazoline amphoteric surfactant selected from the group consisting of cocoamphoacetate, lauroamphoacetate, and mixtures thereof in an amount from about 4% to about 20% by weight, and an additional anionic surfactant selected from the group consisting of an N-methyl cocoyl taurate, a laureth sulfate, and mixtures thereof in an amount from about 5% to about 10% by weight, said composition having a pH between about 7.5 and 8.5 and a viscosity of less than about 10,000 cps.

2. A mixture as claimed in claim 1 wherein the weight ratio of said acyl isethionate to said imidazoline amphoteric surfactant is from about 3:1 to about 1:3.

3. A mixture as claimed in claim 1 wherein the weight ratio of said acyl isethionate to said imidazoline amphoteric surfactant is from about 2:1 to about 1:1.

4. A composition as claimed in claim 1 wherein said acyl isethionate is sodium cocoyl isethionate.

5. A composition as claimed in claim 1 wherein said imidazoline amphoteric surfactant is a cocoamphoacetate.

6. A composition as claimed in claim 1 wherein said imidazoline amphoteric surfactant is sodium cocoamphoacetate.

7. A composition as claimed in claim 1 wherein said imidazoline amphoteric surfactant is a lauroamphoacetate.

8. A composition as claimed in claim 1 wherein said imidazoline amphoteric surfactant is sodium lauroamphoacetate.

9. A composition as claimed in claim 1 wherein said additional anionic surfactant is an N-methyl cocoyl taurate.

10. A composition as claimed in claim 1 wherein said additional anionic surfactant is sodium N-methyl cocoyl taurate.

11. A composition as claimed in claim 1 wherein said additional anionic surfactant is a sodium laureth sulfate.

12. A composition as claimed in claim 1 wherein said additional anionic surfactant is comprised of an N-methyl cocoyl taurate and a laureth sulfate.

13. A composition as claimed in claim 1 wherein said composition has a pH of about 7.8 to about 8.2.

14. A personal care or household detergent care composition comprising the mixture of claim 1.

15. The personal care or household detergent care composition of claim 14 selected from the group consisting of solid or liquid cleaning compositions, shampoos, hand soaps, body washes, dishwashing detergents, fabric detergents and hard surface cleaning compositions.

* * * * *